United States Patent [19]

Mausner

[11] Patent Number: 5,254,331
[45] Date of Patent: Oct. 19, 1993

[54] SKIN CREAM COMPOSITION

[75] Inventor: Jack Mausner, New York, N.Y.

[73] Assignee: Chanel, Inc., New York, N.Y.

[21] Appl. No.: 758,768

[22] Filed: Sep. 12, 1991

[51] Int. Cl.⁵ .................. A61K 7/42; A61K 7/48;
                                           A61K 9/50
[52] U.S. Cl. ................... 424/59; 424/195.1;
            424/401; 514/773; 514/776; 514/777; 514/783;
                                          514/844; 514/847
[58] Field of Search ............ 514/783, 776, 773, 777,
                                    514/844, 847; 424/195, 59

[56] References Cited

U.S. PATENT DOCUMENTS

| | | | |
|---|---|---|---|
| 3,697,643 | 10/1972 | Shepherd et al. | 424/63 |
| 3,864,275 | 2/1975 | Kan et al. | 424/32 |
| 3,911,105 | 10/1975 | Papantoniou et al. | 424/64 |
| 3,966,398 | 6/1976 | Vanlerberghe et al. | 8/11 |
| 4,125,549 | 11/1978 | Coopersmith et al. | 424/64 |
| 4,247,411 | 1/1981 | Vanlerberghe et al. | 252/316 |
| 4,369,037 | 1/1983 | Matsunaga et al. | 8/127.51 |
| 4,423,031 | 12/1983 | Murui et al. | 424/63 |
| 4,440,295 | 8/1983 | Ootsu et al. | 252/356 |
| 4,460,371 | 7/1984 | Abber | 604/897 |
| 4,481,186 | 11/1984 | Deckner | 424/59 |
| 4,549,990 | 10/1985 | Seguin et al. | 260/397.25 |
| 4,608,392 | 8/1986 | Jacquet et al. | 514/844 |
| 4,752,496 | 6/1988 | Fellows et al. | 427/27 |
| 4,758,599 | 7/1988 | Minetti | 514/844 |
| 4,820,510 | 4/1989 | Arraudeau et al. | 424/63 |
| 4,883,659 | 11/1989 | Goodman et al. | 424/78 |
| 4,925,667 | 5/1990 | Fellows et al. | 424/401 |
| 4,927,952 | 5/1990 | Gueyne et al. | 556/419 |
| 4,952,560 | 8/1990 | Kigasawa et al. | 514/2 |
| 4,980,155 | 12/1990 | Shah et al. | 424/63 |
| 4,988,502 | 1/1991 | Ounanian et al. | 424/63 |
| 5,034,226 | 7/1991 | Beck | 424/195.1 |
| 5,037,803 | 8/1991 | Gueyne et al. | 514/2 |
| 5,053,220 | 10/1991 | Arraudeau et al. | 424/63 |
| 5,053,221 | 10/1991 | Robertson et al. | 424/63 |
| 5,061,481 | 10/1991 | Suzuki et al. | |

*Primary Examiner*—Dale E. Ore
*Attorney, Agent, or Firm*—Michael B. Farber

[57] ABSTRACT

A skin cream composition of the present invention comprises: water, and emulsified and dispersed in the water: (1) a protein complex comprising serum proteins and hydrolyzed animal proteins; (2) a protein-amino acid-vitamin-nucleotide complex comprising propylene glycol, serum proteins, niacinamide, water, adenosine phosphate, and arginine; and (3) dimethylsilanoyl hyaluronate complex, and the dimethylsilanoyl hyaluronate are each present in cosmetically effective quantities. Preferably, the skin cream composition further comprises a highly stable micellar complex.

6 Claims, No Drawings

SKIN CREAM COMPOSITION

BACKGROUND

This application is directed to an improved skin cream composition.

Modern environmental conditions, such as heating and air conditioning, exposure to the sun, and environmental pollution exert severe stress on the skin and accelerate the natural aging process, resulting in wrinkles, loss of firmness and elasticity, dryness, and other cosmetically undesirable effects. Although a number of skin cream compositions already exist, there is a need for a simple to apply and effective all-in-one cosmetic treatment, such as a skin cream, that can counteract and minimize simultaneously the stress on the skin, improve firmness and elasticity, counteract dryness, so that wrinkles and other cosmetically undesirable effects appearing on the skin are prevented or delayed, as well as correcting existing wrinkles.

SUMMARY

A skin cream composition according to the present invention meets these needs simultaneously. The skin cream composition of the present invention acts to prevent or correct deleterious effects on the skin such as stress, sensitivity, irritation, wrinkles, improve firmness and elasticity of the skin, and exerts significant improvement of the skin barrier effect against external aggression, resulting in a much less lined and significantly denser, firmer, and smoother skin. Such skin will also be significantly hydrated or moisturized.

The skin cream composition of the present invention comprises: water, and emulsified and dispersed in the water:

(1) a protein complex comprising serum proteins and hydrolyzed animal protein;

(2) a protein-amino acid-vitamin-nucleotide complex comprising propylene glycol, serum proteins, niacinamide, water, adenosine phosphate, and arginine; and (3) dimethylsilanoyl hyaluronate. The protein complex, the protein-amino acid-vitamin-nucleotide complex, and the dimethylsilanoyl hyaluronate are each present in cosmetically effective quantities.

Preferably, the protein complex further comprises glycogen, sodium lactate, sodium pyrrolidone carboxylate and glycerin.

Preferably, the skin cream composition further comprises a micellar complex comprising horse chestnut extract, Crataegus extract, water, panthenol, propylene glycol, phospholipids, phenoxyethanol, glycosphingolipids, chlorphenesin, and cholesterol, wherein the horse chestnut extract comprises from about 9% to about 18% of the micellar complex, the Crataegus extract comprises from about 9% to about 18% of the micellar complex, water comprises from about 24% to about 36% of the micellar complex, the propylene glycol comprises from about 3 to about 9% of the micellar complex, the phospholipids comprise from about 3% to about 9% of the micellar complex, the phenoxyethanol comprises from about 3% to about 9% of the micellar complex, the glycosphingolipids comprise from about 3% to about 9% of the micellar complex, the chlorphenesin comprises from about 3% to about 9% of the micellar complex, and the cholesterol comprises from about 3% to about 9% of the micellar complex, the micellar complex being present in a cosmetically effective quantity.

Most preferably, the protein complex comprises from about 5.1% to about 6.9% of the composition, the protein-amino acid-vitamin-nucleotide complex comprises from about 3.4% to about 4.6% of the composition, and the dimethylsilanoyl hyaluronate comprises from about 5.1% to about 6.9% of the composition. Most preferably, the micellar complex comprises from about 4.25% to about 5.75% of the composition.

In addition to the protein complex, the protein-amino acid-vitamin-nucleotide complex, the dimethylsilanoyl hyaluronate, and the micellar complex, if present, designated the cosmetic components, the skin cream composition of the present invention can further comprise additional ancillary components. These ancillary components can include (1) an oil component; (2) cholesterol; (3) a lipid-soluble component; (4) a complex of dextran, glycine, and glucosamine; (5) a solvent component; (6) a thickener component; (7) glycerin; (8) a complex of propylene glycol, phenoxyethanol, chlorphenesin, and methylparaben; (9) trisodium EDTA; (10) benzophenone-4 and benzophenone-2; (11) a pigment component; and (12) fragrance. Most preferably, the composition of the present invention comprises all of these ancillary components in addition to the cosmetic components.

The oil component can comprise macadamia nut oil, tallow, and a medium-chain fatty acid ester of glycerol selected from the group consisting of glyceryl triheptanoate, glyceryl trioctanoate, glyceryl trinonanoate, and mixtures thereof. Preferably, the medium-chain fatty acid ester of glycerol is glyceryl trioctanoate. Preferably, the macadamia nut oil comprises from about 2.55% to about 3.45% of the composition, the tallow comprises from about 2.85% to about 3.85% of the composition, and the glyceryl trioctanoate comprises from about 6.0% to about 8.0% of the composition Preferably, the cholesterol comprises from about 1.2% to about 1.6% of the composition.

The lipid-soluble component can comprise (1) hydrogenated soy glycerides;

(2) a long-chain fatty acid ester of cetyl alcohol selected from the group consisting of cetyl palmitate, cetyl myristate, cetyl stearate, and mixtures thereof;

(3) an oil based complex comprising palm kernel oil, palm oil, and PEG-6;

(4) palmitoyl hydrolyzed animal protein;

(5) dimethicone;

(6) steareth-2;

(7) a glyceryl ester complex comprising glyceryl linoleate, glyceryl linolenate, and glyceryl arachidonate;

(8) a short-chain fatty acid ester of tocopherol selected from the group consisting of tocopheryl acetate, tocopheryl propionate, tocopheryl butyrate, and mixtures thereof;

(9) a fatty acid ester of ascorbic acid selected from the group consisting of ascorbyl palmitate, ascorbyl myristate, ascorbyl stearate, and mixtures thereof;

(10) an antioxidant component in a quantity sufficient to retard oxidation of the composition;

(11) steareth-21;

(12) cetyl alcohol;

(13) jojoba esters;

(14) a long-chain fatty acid ester of glycerol selected from the group consisting of glyceryl stearate, glyceryl palmitate, glyceryl arachidate, and mixtures thereof;

(15) an arachidyl ester selected from the group consisting of arachidyl propionate, arachidyl acetate, arachidyl butyrate, and mixtures thereof; and

(16) hydrogenated jojoba oil.

Preferably, the long-chain fatty acid ester of cetyl alcohol is cetyl palmitate, the short-chain fatty acid ester of tocopheryl is tocopheryl acetate, the fatty acid of ascorbate is ascorbyl palmitate, the antioxidant component is a mixture of 70% propylene glycol, 20% propyl gallate, and 10% citric acid, the long-chain fatty acid ester of glycerol is glyceryl stearate, and the arachidyl ester is arachidyl propionate. Most preferably, the hydrogenated soy glycerides comprise from about 0.15% to about 0.25% of the composition, the cetyl palmitate comprise from about 0.35% to about 0.45% of the composition, the oil based complex comprises from about 0.95% to about 1.25% of the composition, the palmitoyl hydrolyzed animal protein comprises from about 0.08% to about 0.12% of the composition, the dimethicone comprises from about 1.7% to about 2.3% of the composition, the steareth-2 comprises from about 2.15% to about 2.95% of the composition, the glyceryl ester complex comprises from about 0.7% to about 0.9% of the composition, the tocopheryl acetate comprises from about 0.7% to about 0.9% of the composition, the ascorbyl palmitate comprises from about 0.01% to about 0.03% of the composition, the mixture of propylene glycol, propyl gallate, and citric acid comprises from about 0.08% to about 0.12% of the composition, the steareth-21 comprises from about 1.3% to 1.7% of the composition, the cetyl alcohol comprises from about 1.0% to about 1.4% of the composition, the jojoba esters comprise from about 1.3% to about 1.7% of the composition, the glyceryl stearate comprises from about 0.7% to about 0.9% of the composition, the arachidyl propionate comprises from about 1.1% to 1.5% of the composition, and the hydrogenated jojoba oil comprises from about 1.3% to about 1.7% of the composition.

The skin cream composition of the present invention can further comprise a complex of dextran, glycine, and glucosamine, wherein the dextran is from about 70% to about 90% of the complex, the glycine is from about 10% to about 20% of the complex, and the glucosamine is from about 5% to about 15% of the complex. Preferably, the complex of dextran, glycine, and glucosamine comprises from about 2.55% to about 3.45% of the composition.

The skin cream composition can further comprise a solvent component. The solvent component can be selected from the group consisting of propylene glycol, 1,3-butylene glycol, and mixtures thereof. Preferably, the solvent component is 1,3-butylene glycol. Most preferably, the 1,3-butylene glycol comprises from about 2.35% to about 3.15% of the composition.

The skin cream composition can further comprise a thickener component in a quantity sufficient to retain the composition when it is applied to the face of a wearer. The thickener component can comprise at least one thickener selected from the group consisting of xanthan gum and sodium polyacrylate starch. Preferably, the thickener component comprises both xanthan gum and sodium polyacrylate starch, the xanthan gum comprising from about 0.08% to about 0.12% of the composition and the sodium polyacrylate starch comprising from about 0.09% to about 0.13% of the composition.

The skin cream composition of the present invention can further comprise glycerin. Preferably, the glycerin comprises from about 2.55% to about 3.45% of the composition.

The skin cream composition can further comprise a complex of propylene glycol, phenoxyethanol, chlorphenesin, and methylparaben, wherein the propylene glycol is from about 30% to about 45% of the complex, the phenoxyethanol is from about 22% to about 37% of the complex, the chlorphenesin is from about 11% to about 22% of the complex, and the methylparaben is from about 11% to about 22% of the complex. Preferably, the complex of propylene glycol, phenoxyethanol, chlorphenesin, and methylparaben comprises from about 2.1% to about 2.9% of the composition.

The skin cream composition can further comprise trisodium EDTA. Preferably, the trisodium EDTA comprises from about 0.3% to about 0.7% of the composition.

The skin cream composition can further comprise benzophenone-4 and benzophenone-2. Preferably, the benzophenone-4 comprises from about 0.40% to 0.55% of the composition, and the benzophenone-2 comprises from about 0.02% to about 0.04% of the composition.

The skin cream composition can further comprise a pigment component. The pigment component can comprise at least one pigment selected from the group consisting of titanium dioxide, D&C Red #30 Lake, and FD&C Yellow #6 Aluminum Lake. Preferably, the pigment component comprises all of titanium dioxide, D&C Red #30 Lake, and FD&C Yellow #6 Aluminum Lake, the titanium dioxide comprising from about 1.05% to 1.45% of the composition, the D&C Red #30 Lake comprising from about 0.003% to about 0.007% of the composition, and the FD&C Yellow #6 Aluminum Lake comprising from about 0.005% to about 0.010% of the composition.

The skin cream composition of the present invention can further comprise fragrance as is commonly used in the cosmetic art. Preferably, the fragrance comprises from about 0.7% to about 0.9% of the composition.

The skin cream composition of the present invention can be formulated to exert one or more of the following desirable effects on the skin: (i) anti-stress, calming, and soothing effects; (ii) moisturizing and hydrating effects; (iii) firming and elasticity promoting effects; and (iv) anti-wrinkle effects. The composition can be formulated to exert all of these effects.

A preferred skin cream composition according to the present invention comprises: water, and emulsified and dispersed in the water:

(1) about 2.55% to about 3 45% of macadamia nut oil;

(2) about 2.85% to about 3.85% of tallow;

(3) about 6.0% to about 8.0% of glyceryl trioctanoate;

(4) about 1.2% to about 1.6% of cholesterol;

(5) about 1.2% to about 1.6% of hydrogenated soy glycerides;

(6) about 0.35% to about 0.5% of cetyl palmitate;

(7) about 0.95% to about 1.25% of a complex of palm kernel oil, palm oil, and PEG-6;

(8) about 0.08% to 0.12% of palmitoyl hydrolyzed animal protein;

(9) about 1.7% to about 2.3% of dimethicone;

(10) about 2.15% to about 2.95% of steareth-2;

(11) about 0.7% to about 0.9% of a glyceryl ester complex comprising glyceryl linoleate, glyceryl linolenate, and glyceryl arachidonate;

(12) about 0.7% to about 0.9% of tocopheryl acetate;

(13) about 0.01% to about 0.03% of ascorbyl palmitate;

(14) about 0.08% to about 0.12% of a mixture of 70% propylene glycol, 20% propyl gallate, and 10% citric acid;

(15) about 1.3% to about 1.7% of steareth-21;

(16) about 1.0% to 1.4% of cetyl alcohol;

(17) about 1.3% to 1.7% jojoba esters;

(18) about 0.7% to 0.9% glyceryl stearate;

(19) about 1.1% to about 1.5% of arachidyl propionate; (20) about 1.3% to about 1.7% of hydrogenated jojoba oil;

(21) about 5.1% to 6 9% of dimethylsilanoyl hyaluronate;

(22) about 3.4% to 4.6% of a protein-amino acid-vitamin-nucleotide complex comprising propylene glycol, serum proteins, niacinamide, water, adenosine phosphate, and arginine;

(23) about 5.1% to about 6.9% of a protein complex comprising serum proteins, hydrolyzed animal protein, glycogen, sodium lactate, sodium pyrrolidone carboxylate, and glycerin;

(24) about 2.55% to about 3.45% of a complex of dextran, glycine, and glucosamine, wherein the dextran is from about 70% to about 90% of the complex, the glycine is from about 10% to about 20% of the complex, and the glucosamine is from about 5% to about 15% of the complex;

(25) about 2.35% to about 3.15% of 1,3-butylene glycol;

(26) about 0.08% to about 0.12% of xanthan gum;

(27) about 0.09% to 0.13% of sodium polyacrylate starch;

(28) about 2.55% to about 2.45% of glycerin;

(29) about 2.1% to about 2.9% of a complex of propylene glycol, phenoxyethanol, chlorphenesin, and methylparaben, wherein the propylene glycol is from about 30% to about 45% of the complex, the phenoxyethanol is from about 22% to about 37% of the complex, the chlorphenesin is from about 11% to about 22% of the complex, and the methylparaben is from about 11% to about 22% of the complex;

(30) about 0.03% to about 0.07% of trisodium EDTA;

(31) about 0.40% to about 0 55% of benzophenone-4;

(32) about 0.02% to 0.04% of benzophenone-2;

(33) about 1.05% to about 1.45% of titanium dioxide;

(34) about 0.7% to about 0.9% of fragrance;

(35) about 4.25% to about 5.7% of a micellar complex comprising horse chestnut extract, Crataegus extract, water, panthenol, propylene glycol, phospholipids, phenoxyethanol, glycosphingolipids, chlorphenesin, and cholesterol, wherein the horse chestnut extract comprises from about 9% to about 18% of the micellar complex, the Crataegus extract comprises from about 9% to about 18% of the micellar complex, water comprises from about 24% to about 36% of the micellar complex, the propylene glycol comprises from about 3% to about 9% of the micellar complex, the phospholipids comprise from about 3% to about 9% of the micellar complex, the phenoxyethanol comprises from about 3% to about 9% of the micellar complex, the glycosphingolipids comprise from about 3% to about 9% of the micellar complex, the chlorphenesin comprises from about 3% to about 9% of the micellar complex, and the cholesterol comprises from about 3% to about 9% of the micellar complex;

(36) about 0.03% to about 0.07% of D&C Red #30 Lake; and

(37) about 0.005% to about 0.01% of FD&C Yellow #6 Aluminum Lake.

DESCRIPTION

A new combination of ingredients results in a skin cream that simultaneously exerts a significant wrinkle corrective effect and firming of the skin improving its elasticity as well as promoting a significant improvement of the skin barrier effect against external aggression. The skin cream of the present invention at the same time further exerts a significant soothing, calming, and healing effect, as well as highly significant hydrating and moisturizing effects on the skin, with up to a 300% increase in hydration observed The skin cream composition of the present invention comprises an aqueous base in which cosmetic components are emulsified and dispersed. The composition preferably also comprises a micellar complex containing lipids, panthenol, and plant extracts, the micelles being colloidal vectors with an average particle size of less than about 0.001 mm. This represents a major innovation in a carrier system, enabling these smaller particles to penetrate deeper into the skin than possible hitherto, e g , with liposomes. They are also significantly more stable than liposomes and thus much more effective. Optimally, the skin cream composition can also comprise ancillary components such as: (1) an oil component; (2) cholesterol; (3) a lipid-soluble component; (4) a complex of dextran, glycine, and glucosamine; (5) a solvent component; (6) a thickener component; (7) glycerin; (8) a complex of propylene glycol, phenoxyethanol, chlorphenesin, and methylparaben; (9) trisodium EDTA; (10) benzophenone-4 and benzophenone-2; (11) a pigment component; and (12) fragrance.

The ingredients are dispersed in an emulsified composition by the method of preparation discussed below. "Dispersal" refers to any process by which the ingredients are uniformly distributed in the emulsified base, and includes dissolving, emulsifying, and forming a colloidal suspension.

I. NATURE AND PROPORTION OF INGREDIENTS OF THE SKIN CREAM COMPOSITION

A. The Cosmetic Components

The cosmetic components include (1) a protein complex; (2) a protein-amino acid-vitamin-nucleotide complex; and (3) dimethylsilanoyl hyaluronate. Each of these components contributes to the improved properties of the skin cream composition of the present invention and is present in a cosmetically effective quantity.

1. The Protein Complex

The protein complex comprises serum proteins and hydrolyzed animal protein. Although applicant does not intend to be bound by this theory, it is believed that these components counteract the loss of essential ground substance due to the normal aging process These components are believed to provide volume and bulk to result in a denser and firmer skin. Preferably, the protein complex further comprises glycogen, sodium lactate, sodium pyrrolidone carboxylate, and glycerin.

Preferably, the serum proteins come from human serum, such as the albumin or globulin fractions Preferably, the hydrolyzed animal protein comes from a source such as bovine, ovine, or porcine protein. Preferably, the protein complex comprises from about 21% to about 28% serum protein, from about 22% to about 30% hydrolyzed animal protein, from about 4% to about 6% glycogen, from about 6% to about 8% of sodium lactate, from about 6% to about 8% sodium pyrrolidone carboxylate, and from about 25% to about 35% glycerin. Most preferably, the protein complex comprises from about 5.1% to about 6.9% of the skin cream composition.

An example of a suitable protein complex is Iconoderm LS 1054B, commercially available from Lab Serobiologique, Inc., Somerville, N.J. This complex comprises 25% serum proteins (with a range of 21% to 29%), 26% hydrolyzed animal protein (with a range of 22% to 30%), 5% glycogen (with a range of 4% to 6%), 7% sodium lactate (with a range of 6% to 8%), 30% glycerin (with a range of 25% to 35%), and 7% sodium pyrrolidone carboxylate (with a range of 6% to 8%).

2. The Protein-Amino Acid-Vitamin-Nucleotide Complex

The protein-amino acid-vitamin-nucleotide complex comprises propylene glycol, serum proteins, niacinamide, water, adenosine phosphate, and arginine. Although applicant does not intend to be bound by this theory, it is believed that these components act to stimulate the regeneration of epidermal cells and stimulate the activity of fibroblasts to produce a thickening effect of the epidermis similar to that seen with retinoic acid. This effect is believed to be responsible for making the skin more elastic, smoother, and firmer. Preferably, the protein-amino acid-vitamin-nucleotide complex comprises from about 30% to about 50% propylene glycol, from about 25% to about 35% serum proteins, from about 10% to about 20% niacinamide, from about 10% to about 20% adenosine phosphate, and from about 10% to about 20% arginine. Preferably, the protein-amino acid-vitamin-nucleotide complex comprises from about 3.4% to about 4.6% of the skin cream composition.

An example of a suitable protein-amino acid-vitamin-nucleotide complex is Trilogie TLG LS 6309, commercially available from Lab Serobiologique, Inc., Somerville, N.J.

3. Dimethylsilanoyl Hyaluronate

Dimethyl hyaluronate is a derivative of hyaluronic acid, a mucopolysaccharide major component of the ground substance of the skin. Preferably, dimethylsilanoyl hyaluronate comprises from about 5.1% to about 6.9% of the composition. This ingredient is believed to exert a strong moisturizing effect, significantly increasing the water content of the skin.

B. Micellar Complex

The micellar complex comprises horse chestnut extract, Crataegus (hawthorne blossom) extract, water, panthenol, propylene glycol, phospholipids, phenoxyethanol, glycosphingolipids, and cholesterol. The micellar complex, when present, is present in a cosmetically effective quantity in order to significantly hydrate and moisturize the skin as well as to provide substantial healing, soothing, calming, and anti-irritant activities.

The micelles are colloidal vectors with an average particle size of less than 0.001 mm, and are stable globular structures formed by lipids oriented such that polar head groups are on the surface and their hydrocarbon tails are sequestered in the interior of the micelle. They are much smaller than any previously used "capsules" in cosmetics, e.g., liposomes, and can therefore penetrate the skin faster and to greater depth. They are also much more stable than liposomes and therefore much more effective.

The horse chestnut extract and Crataegus extract are plant extracts that are believed to exert anti-stress, anti-inflammatory effects, calming, and soothing.

Panthenol is the racemic dl-form of 2,4-dihydroxy-N-(3-hydroxypropyl)-3,3-dimethylbutanamide, and is also known as Vitamin $B_5$. It is believed to exert a calming, soothing and protective effect on the skin. The phospholipids can be phosphatidyl ethanolamine, phosphatidyl choline, phosphatidyl serine, phosphatidyl inositol, or diphosphatidyl glycerol.

Glycosphingolipids comprise ceramide covalently bound to carbohydrate on the primary hydroxyl group of the ceramide. The carbohydrate is typically glucose, lactose, N-acetylglucosamine, N-acetylgalactosamine or sialic acid.

The glycosphingolipids are believed to have a powerful hydrating effect, together with the ability to restructure and reinforce the barrier effect of the skin and improve the cohesion of the corneocytes. They are also believed to have an overall soothing effect and to exert a protective role against environmental aggression Preferably the horse chestnut extract comprises from about 9% to about 18% of the micellar complex, the Crataegus extract comprises from about 9% to about 18% of the micellar complex, water comprises from about 24% to about 36% of the micellar complex, the propylene glycol comprises from about 3% to about 9% of the micellar complex, the phospholipids comprise about 3% to about 9% of the micellar complex, the glycosphingolipids comprise about 3% to about 9% of the micellar complex, the chlorphenesin comprises about 3% to about 9% of the micellar complex, and the cholesterol comprises about 3% to about 9% of the micellar complex. Preferably, the micellar complex comprises from about 4.25% to about 5.75% of the composition.

An example of a suitable micellar complex is Micelles Leniplex LS 6309, commercially available from Lab Serobiologique, Inc., Somerville, N.J.

C. The Ancillary Components

The ancillary components, whose use is optional but preferable, impart additional desirable properties to the skin cream composition of the present invention. These components can include: (1) an oil component; (2) cholesterol; (3) a lipid-soluble component; (4) a complex of dextran, glycine, and glucosamine; (5) a solvent component; (6) a thickener component; (7) glycerine; (8) a complex of propylene glycol, phenoxyethanol, chlorphenesin, and methylparaben; (9) trisodium EDTA; (10) benzophenone-4 and benzophenone-2; (11) a pigment component; and (12) fragrance. Preferably, the composition of the present invention comprises all the ancillary components as indicated below.

1. The Oil Component

The oil component can comprise macadamia nut oil, tallow, and a medium-chain fatty acid ester of glycerol selected from the group consisting of glyceryl triheptanoate, glyceryl trioctanoate, glyceryl trinonanoate, and mixtures thereof. Most preferably, the medium-chain fatty acid ester of glycerol is glyceryl trioctanoate. Most preferably, the macadamia nut oil comprises from about 2.55% to about 3.45% of the composition, the tallow comprises from about 2.85% to about 3.85% of the composition, and the glyceryl trioctanoate comprises from about 6.0% to about 8.0% of the composition.

2. Cholesterol

The skin cream composition of the present invention can further comprise cholesterol. Cholesterol can comprise from about 1.2% to about 1.6% of the composition.

3. The Lipid-Soluble Component

The lipid-soluble component can comprise any of these ingredients as follows: (a) hydrogenated soy glycerides; (b) a long-chain fatty acid ester of cetyl alcohol; (c) an oil-based complex; (d) palmitoyl hydrolyzed animal protein; (e) dimethicone; (f) steareth-2; (g) a glyceryl ester complex; (h) a short-chain fatty acid of tocopherol; (i) a fatty acid ester of ascorbic acid; (j) an antioxidant component; (k) steareth-21; (l) cetyl alcohol; (m) jojoba esters; (n) a long-chain fatty acid ester of glycerol; (o) an arachidyl ester; and (p) hydrogenated jojoba oil.

The long-chain fatty acid ester of cetyl alcohol can be selected from the group consisting of cetyl palmitate, cetyl myristate, cetyl stearate, and mixtures thereof. Preferably, the long-chain fatty acid ester of cetyl alcohol is cetyl palmitate.

The oil-based complex comprises palm kernel oil, palm oil, and PEG-6. In the oil-based complex, the palm kernel oil comprises from about 40% to about 60% of the complex, the palm oil comprises from about 30% to about 40% of the complex, and the PEG-6 comprises from about 12% to about 18% of the complex. A suitable oil-based complex is Labrafil M2130, commercially available from Gattefosse Corporation of Elmford, N.Y.

The glyceryl ester complex comprises glyceryl linoleate, glyceryl linolenate, and glyceryl arachidonate. In the complex, the glyceryl linoleate comprises from about 65% to about 85% of the complex, the glyceryl linolenate comprises from about 5% to about 15% of the complex, and the glyceryl arachidonate comprises from about 1% to about 5% of the complex.

The short-chain fatty acid ester of tocopherol can be selected from the group consisting of tocopheryl acetate, tocopheryl propionate, tocopheryl butyrate, and mixtures thereof. Preferably, the short-chain fatty acid ester of tocopherol is tocopheryl acetate.

The fatty acid ester of ascorbic acid can be selected from the group consisting of ascorbyl palmitate, ascorbyl myristate, ascorbyl stearate, and mixtures thereof. Preferably, the fatty acid ester of ascorbic acid is ascorbic palmitate.

The long-chain fatty acid ester of glycerol can be selected from the group consisting of glyceryl stearate, glyceryl palmitate, glyceryl arachidate, and mixtures thereof. Preferably, the long-chain fatty acid ester of glycerol is glyceryl stearate.

The arachidyl ester can be selected from the group consisting of arachidyl propionate, arachidyl acetate, arachidyl butyrate, and mixtures thereof. Preferably, the arachidyl ester is arachidyl propionate.

Steareth-2 is polyoxyethylene (2) stearylether with 0.01% butylated hydroxyanisole and 0.005% citric acid added as preservatives. Similarly, steareth-21 is polyoxyethylene (21) stearylether with 0.01% butylated hydroxyanisole and 0.005% citric acid added as preservatives.

The antioxidant component prevents oxidation of the ingredients of the composition. The antioxidant component can be a mixture of 70% propylene glycol, 20% propyl gallate, and 10% citric acid. A suitable mixture of propylene glycol, propyl gallate and citric acid in these proportions is available under the trademark of Tenox S-1 TM, manufactured by Eastman Kodak of Rochester, N.Y.

Preferably, the lipid-soluble component comprises all the above listed ingredients. Most preferably, the ingredients of the lipid-soluble component are present in the following proportions: hydrogenated soy glycerides from about 0.15 % to about 0.25 % of the composition; cetyl palmitate from about 0.35% to about 0.45% of the composition, the oil-based complex from about 0.95% to about 1.25% of the composition; palmitoyl hydrolyzed animal protein from about 0.08% to about 0.12% of the composition; dimethicone from about 1.7% to about 2.3% of the composition; steareth-2 from 2.15% to about 2.95% of the composition; glyceryl ester complex from about 0.7% to about 0.9% of the composition; tocopheryl acetate from about 0.7% to about 0.9% of the composition; ascorbyl palmitate from about 0.01% to about 0.3% of the composition; the mixture of propylene glycol, propyl gallate, and citric acid from about 0.08% to about 0.12% of the composition; steareth-21 from about 1.3% to about 1.7 percent of the composition; cetyl alcohol from about 1.0% to about 1.4% of the composition; jojoba esters from about 1.3% to about 1.7% of the composition; glycerol stearate from about 0.7% to about 0.9% of the composition; arachidyl propionate from about 1.1% to about 1.5% of the composition; and hydrogenated jojoba oil from about 1.3% to about 1.7% of the composition.

4. The Complex of Dextran, Glycine, and Glucosamine

The skin cream composition of the present invention can further comprise a complex of dextran, glycine, and glucosamine wherein the dextran is from about 70% to about 90% of the complex, the glycine is from about 10% to about 20% of the complex, and the glucosamine is from about 5% to about 15% of the complex. Preferably, the complex of dextran, glycine, and glucosamine comprises from about 2.55% to about 3.45% of the composition. A suitable complex of dextran, glycine, and glucosamine is Thalassamine LS 80/98, commercially available from Lab Serobiologique, Inc., Somerville, N.J.

5. The Solvent Component

The skin cream composition can comprise a solvent component for greater uniformity and ease of preparation. The solvent component can be selected from the group consisting of propylene glycol, 1,3-butylene glycol, and mixtures thereof. Preferably, the solvent component is 1,3-butylene glycol. Most preferably, the 1,3-butylene glycol comprises from about 2.35% to about 3.15% of the composition.

6. The Thickener Component

The skin cream composition can comprise a thickener component in a quantity sufficient to retain the composition when it is applied to the face of a wearer. The thickener component can comprise at least one thickener selected from the group consisting of xanthan gum and sodium polyacrylate starch. Preferably the thickener component comprises both xanthan gum and sodium polyacrylate starch. Most preferably, the xanthan gum comprises from about 0.08% to about 0.12% of the composition and the sodium polyacrylate starch comprises from about 0.09% to about 0.13% of the composition.

7. Glycerin

The skin cream composition of the present invention can further comprise glycerin to improve the smoothness and feel of the composition. Preferably, the glycerin comprises from about 2.55% to about 3.45% of the composition.

8. The Complex of Propylene Glycol, Phenoxyethanol, Chlorphenesin, and Methylparaben The composition can further comprise a complex of propylene glycol, phenoxyethanol, chlorphenesin, and methylparaben to retard microbial and mold growth in the composition, which is typically manufactured under clean but non-sterile conditions. The propylene glycol comprises from about 30% to about 45% of the complex, the phenoxyethanol comprises from about 22% to about 37% of the complex, the chlorphenesin comprises from about 11% to about 22% of the complex, and the methylparaben comprises from about 11% to about 22% of the complex. Preferably, the complex of propylene glycol, phenoxyethanol, chlorphenesin, and methylparaben comprises from about 2.1% to about 2.9% of the composition. A suitable complex of propylene glycol, phenoxyethanol, chlorphenesin, and methylparaben is available as Elestab 388 from Lab Serobiologique, Inc. of Somerville, N.J.

9. Trisodium EDTA

The skin cream composition of the present invention can further comprise trisodium EDTA to enhance the shelf life of the composition. Preferably, the trisodium EDTA comprises from about 0.3% to about 0.7% of the composition.

10. Benzophenone-4 and Benzophenone-2

The composition can further comprise benzophenone-4 and benzophenone-2, which exert a protective effect by screening out ultraviolet rays. Preferably, the benzophenone-4 comprises from about 0.40% to about 0.55% of the composition, and the benzophenone-2 comprises from about 0.02% to about 0.04% of the composition.

11. The Pigment Component

The skin cream composition of the present invention can further comprise a pigment component to give the skin cream an aesthetically desirable appearance. The pigment component can comprise at least one pigment selected from the group consisting of titanium dioxide, D&C Red #30 Lake, and FD&C Yellow #6 Aluminum Lake. Preferably, the pigment component comprises titanium dioxide, D&C Red #30 Lake, and FD&C Yellow #6 Aluminum Lake. Most preferably, the titanium dioxide comprises from about 1.05% to about 1.45% of the composition, the D&C Red #30 Lake comprises from about 0.003% to about 0.007% of the composition, and the FD&C Yellow #6 Aluminum Lake comprises from about 0.005% to about 0.010% of the composition.

12. The Fragrance

The skin cream composition of the present invention can further comprise fragrance. Preferably, the fragrance comprises from about 0.7% to about 0.9% of the composition. The fragrance used is a conventional cosmetic fragrance chosen to impart the desired olfactory properties to the skin cream composition. The use of fragrance is well known in the cosmetic art.

The skin cream composition of the present invention can be formulated by adjustment of the proportions of the cosmetic components to exert one or more of the following desirable effects on the skin: (1) anti-stress, calming, soothing, and healing effects; (2) moisturizing and hydrating effects; (3) firming and elasticity promoting effects; and (4) anti-wrinkle effects.

The preferred concentrations of both the cosmetic components and the ancillary components are shown in Table I. Also shown in Table I are the mixtures of which each component is a part for the preparation of the composition as discussed below.

TABLE I

| Mixture | Component | Percentage Range |
|---|---|---|
| INGREDIENTS OF A PREFERRED SKIN CREAM COMPOSITION OF THE PRESENT INVENTION | | |
| I | Macadamia Nut Oil | 2.55–3.45 |
| I | Tallow | 2.85–3.85 |
| I | Glyceryl Trioctanoate | 6.00–8.00 |
| II | Cholesterol | 1.20–1.60 |
| III | Hydrogenated Soy Glycerides | 0.15–0.25 |
| III | Cetyl Palmitate | 0.35–0.45 |
| III | Complex of Palm Kernel Oil, Palm Oil, and PEG-6 | 0.95–1.25 |
| III | Palmitoyl Hydrolyzed Animal Protein | 0.08–0.12 |
| III | Dimethicone | 1.70–2.30 |
| III | Steareth-2 | 2.15–2.95 |
| III | Complex of Glyceryl Linoleate, Glyceryl Linolenate, and Glyceryl Arachidonate | 0.70–0.90 |
| III | Tocopheryl Acetate | 0.70–0.90 |
| III | Ascorbyl Palmitate | 0.01–0.03 |
| III | Tenox S-1 TM | 0.08–0.12 |
| III | Steareth-21 | 1.30–1.70 |
| III | Cetyl Alcohol | 1.00–1.40 |
| III | Jojoba Esters | 1.30–1.70 |
| III | Glyceryl Stearate | 0.70–0.90 |
| III | Arachidyl Propionate | 1.10–1.50 |
| III | Hydrogenated Jojoba Oil | 1.30–1.70 |
| IV | Dimethylsilanoyl Hyaluronate | 5.10–6.90 |
| IV | Complex of propylene Glycol, Serum Proteins, Niacinamide, Water, Adenosine Phosphate, and Arginine | 3.40–4.60 |
| V | Complex of Serum Proteins, Hydrolyzed Animal Protein, Glycogen, Sdium Lactate, Sodium Pyrrolidone Carboxylate, and Glycerin | 5.10–6.90 |
| VI | Complex of Dextran, Glycine, and Glucosamine | 2.55–3.45 |
| VII | 1,3-Butylene Glycol | 2.35–3.15 |
| VIII | Xanthan Gum | 0.08–0.12 |
| VIII | Sodium Polyacrylate Starch | 0.09–0.13 |
| IX | Demineralized Water | 25.90–35.10 |
| X | Glycerin | 2.55–3.45 |
| X | Complex of Propylene Glycol, Phenoxyethanol, Chlorphenesin, and Methylparaben | 2.10–2.90 |
| XI | Trisodium EDTA | 0.03–0.07 |
| XII | Benzophenone-4 | 0.40–0.55 |
| XII | Benzophenone-2 | 0.02–0.04 |
| XIII | Titanium Dioxide | 1.05–1.45 |
| XIII | Demineralized Water | 3.20–4.30 |
| XIV | Fragrance | 0.70–0.90 |

TABLE I-continued

INGREDIENTS OF A PREFERRED SKIN CREAM COMPOSITION OF THE PRESENT INVENTION

| Mixture | Component | Percentage Range |
|---|---|---|
| XV | Micellar Complex of Horse Chestnut Extract Crataegus Extract, Water, Panthenol, Propylene Glycol, Phospholipids, Phenoxyethanol, Glycosphingolipids, Chlorphenesin, and Cholesterol | 4.25-5.75 |
| XVI | D&C Red #30 Lake | 0.003-0.007 |
| XVI | FD&C Yellow #6 Aluminum Lake | 0.005-0.010 |

II. PREPARATION OF THE SKIN CREAM COMPOSITION

The various mixtures in the sequences in which they are prepared and combined for the preparation of the skin cream composition of the present invention are now described in some detail.

Mixtures IV (dimethylsilanoyl hyaluronate and the complex of propylene glycol, serum proteins, niacinamide, water, adenosine phosphate and arginine) and V (the complex of serum proteins, hydrolyzed animal protein, glycogen, sodium lactate, sodium pyrrolidone carboxylate, and glycogen) are introduced into a stainless steel kettle equipped with a high-speed mixer such as a Lightnin' TM Mixer and mixing is begun at moderate speed. Mixture VI (the complex of dextran, glycine, and glucosamine) is then sprinkled into the combination of Mixtures IV and V and mixing is continued until uniform.

Mixture VII (1,3-butylene glycol) and Mixture VIII (xanthan gum and sodium polyacrylate starch) are premixed to form a slurry and then added to Mixtures IV-VI with moderate mixing. Mixing is maintained for one-half hour to form a combined gel phase, which is then set aside for later use.

Separately, Mixture I (macadamia nut oil, tallow, and glycerol trioctanoate), Mixture II (cholesterol) and Mixture III (sixteen ingredients of the lipid-soluble component; see Table I) are charged into a steam-jacketed steel kettle equipped with homogenization mixing and sweep mixing and large enough to hold the entire batch. Mixtures I-III form the oil phase. The oil phase is heated to 80°-85° C. with slow sweep mixing until completely liquified.

Mixtures IX (demineralized water), X (glycerin and the complex of propylene glycol, phenoxyethanol, chlorphenesin and methylparaben), XI (trisodium EDTA), and XII (benzophenone-4 and benzophenone-2) are added at 80°-85° C. to the batch kettle containing mixtures I-III (the oil phase) at 80°-85° C. and homogenization mixing is begun at fast speed together with slow speed sweep mixing. Homogenization mixing is continued at 80°-85° C. for ten minutes, then the contents are cooled using slow homogenization mixing and sweep mixing. The contents are cooled to 50° C. at a rate of 1° C./3 minutes. When the batch has cooled to 50° C., the combined gel phase (Mixtures IV-VIII) are added to the batch kettle with fast speed homogenization mixing for five minutes.

Mixture XIII (titanium dioxide and demineralized water) is mixed together separately, with a high speed mixer such as a Lightnin' TM Mixer until uniform and then added to the batch kettle at 50° C with fast speed homogenization mixing for ten minutes.

Mixture XIV (fragrance) is then added to the batch kettle at 50° C. with fast speed homogenization mixing for two minutes. Homogenization is then discontinued, but moderate sweep mixing is continued.

The batch is cooled to 40° C., and then Mixture XV (the micellar complex) is added with slow to moderate sweep mixing until uniform.

The batch is cooled to 20° C. with moderate sweep mixing, then colored to standard with Mixture XVI (D&C Red #30 Lake and FD&C Yellow #6 Aluminum Lake) and filled into storage vessels for cold room storage (15°-20° C.).

ADVANTAGES OF THE INVENTION

The skin cream composition of the present invention acts simultaneously to prevent and correct wrinkles and exert significant improvement of the skin barrier effect against external aggression. Additionally, at the same time, it exerts a powerful firming effect and improves the elasticity of the skin, with 71% of users demonstrating a significant increase in firmness of the skin. Furthermore, it exerts significant soothing, calming and healing effects and provides substantial hydrating and moisturizing effects on the skin, with up to a 300% increase in water content of the skin recorded. Use of the skin cream composition of the present invention results in a much less lined and significantly denser, firmer, more elastic, and smoother skin. A one-month trial showed approximately a 23% reduction of wrinkles for users of the skin cream of the present invention.

The invention contains a totally new carrier system referred to as micelles. These are capsules whose composition is described herein and which comprise particles of much smaller size than any capsules used in cosmetics before, e.g., liposomes. They are also much more stable. They therefore offer the advantages of faster, deeper penetration into the skin than possible hitherto (e.g., with liposomes), and greater efficacy as a result.

Although the present invention has been described in considerable detail with regard to certain preferred versions thereof, other versions are possible. Therefore, the spirit and scope of the appended claims should not be limited to the description of the preferred versions contained herein.

I claim:

1. An emulsified emollient skin cream composition comprising: water, and emulsified and dispersed in the water:
   (a) a protein complex comprising:
      (i) human serum proteins comprising at least one protein fraction selected from the group consisting of the albumin fraction and the globulin fraction; and
      (ii) hydrolyzed animal protein comprising at least one hydrolyzed protein selected from the group consisting of hydrolyzed bovine protein, hydrolyzed porcine protein, and hydrolyzed ovine protein;
   (b) a protein-arginine-niacinamide-adenosine phosphate complex comprising propylene glycol, serum proteins, niacinamide, water, adenosine phosphate, and arginine;
   (c) dimethylsilanoyl hyaluronate; and
   (d) at least one emulsifying agent; the protein complex comprising from about 5.1% to about 6.9% of the composition, the protein-arginine-niacinamide-adenosine phosphate complex comprising from about 3.4% to about 4.6% of the composition, the dimethylsilanoyl hyaluronate comprising from about 5.1% to about 6.9% of the composition, (k) the emulsifying agent being present in a quantity sufficient to emulsify and disperse the protein complex, the protein-arginine-niacinamide-adenosine phosphate complex, and the dimethylsilanoyl hyaluronate, with water comprising the remainder of the skin cream composition.

2. The skin cream composition of claim 1 wherein the protein complex further comprises glycogen, sodium lactate, sodium pyrrolidone carboxylate, and glycerin.

3. The skin cream composition of claim 1 wherein the at least one emulsifying agent is selected from the group consisting of hydrogenated soy glycerides, dimethicone, steareth-2, and a glyceryl ester complex comprising glyceryl linoleate, glyceryl linolenate, and glyceryl arachidonate.

4. The skin cream composition of claim 1 further comprising:
(e) a micellar complex comprising horse chestnut extract, Crataegus extract, water, panthenol, propylene glycol, phospholipids, phenoxyethanol, glycosphingolipids, chlorphenesin, and cholesterol, wherein the horse chestnut extract comprises from about 9% to about 18% of the micellar complex, the Crataegus extract comprises from about 9% to about 18% of the micellar complex, water comprises from about 24% to about 36% of the micellar complex, the propylene glycol comprises from about 3% to about 9% of the micellar complex, the phospholipids comprise from about 3% to about 9% of the micellar complex, the phenoxyethanol comprises from about 3% to about 9% of the micellar complex, the glycosphingolipids comprise from about 3% to about 9% of the micellar complex, the chlorphenesin comprises from about 3% to about 9% of the micellar complex, and the cholesterol comprises from about 3% to about 9% of the micellar complex, the micellar complex comprising from about 4.25% to about 5.7% of the composition.

5. The skin cream composition of claim 3 wherein the protein complex further comprises glycogen, sodium lactate, sodium pyrrolidone carboxylate, and glycerin.

6. An emulsified emollient skin cream composition comprising: water, and emulsified and dispersed in the water:
(a) about 2.55% to about 3.45% of macadamia nut oil;
(b) about 2.85% to about 3.85% of tallow;
(c) about 6.0% to about 8.0% of glyceryl trioctanoate;
(d) about 1.2% to about 1.6% of cholesterol;
(e) about 1.2% to about 1.6% of hydrogenated soy glycerides;
(f) about 0.35% to about 0.5% of cetyl palmitate;
(g) about 0.95% to about 1.25% of a complex of palm kernel oil, palm oil, and PEG-6;
(h) about 0.08% to about 0.12% of palmitoyl hydrolyzed animal protein;
(i) about 1.7% to about 2.3% of dimethicone;
(j) about 2.15% to about 2.95% of steareth-2;
(k) about 0.7% to about 0.9% of a glyceryl ester complex, comprising glyceryl linoleate, glyceryl linolenate, and glyceryl arachidonate;
(l) about 0.7% to about 0.9% of tocopheryl acetate;
(m) about 0.7% to about 0.03% of ascorbyl palmitate;
(n) about 0.08% to about 0.12% of a mixture of 70% propylene glycol, 20% propyl gallate, and 10% citric acid;
(o) about 1.3% to about 1.7% of steareth-21;
(p) about 1.0% to about 1.4% of cetyl alcohol;
(q) about 1.3% to about 1.7% of jojoba esters;
(s) about 0.7% to about 0.9% of glyceryl stearate;
(t) about 1.3% to about 1.7% of hydrogenated jojoba oil;
(u) about 5.1% to about 6.9% of dimethylsilanoyl hyaluronate;
(v) about 3.4% to about 4.6% of a protein-arginine-niacinamide-adenosine phosphate complex comprising propylene glycol, serum proteins, niacinamide, water, adenosine phosphate, and arginine;
(w) about 5.1% to about 6.9% of a protein complex comprising:
 (i) human serum proteins comprising at least one protein fraction selected from the group consisting of the albumin fraction and the globulin fraction;
 (ii) hydrolyzed animal protein comprising at least one hydrolyzed protein selected from the group consisting of hydrolyzed bovine protein, hydrolyzed porcine protein, and hydrolyzed ovine protein;
 (iii) glycogen;
 (iv) sodium lactate;
 (v) sodium pyrrolidone carboxylate; and
 (vi) glycerin;
(x) about 2.55% to about 3.45% of a complex of dextran, glycine, and glucosamine, wherein the dextran is from about 70% to about 90% of the complex, the glycine is from about 10% to about 20% of the complex, and the glucosamine is from about 5% to about 15% of the complex;
(y) about 2.35% to about 3.15% of 1,3-butylene glycol;
(z) about 0.08% to about 0.12% of xanthan gum;
(aa) about 0.09% to about 0.13% of sodium polyacrylate starch;
(bb) about 2.55% to about 3.45% of glycerine;
(cc) about 2.1% to about 2.9% of a complex of propylene glycol, phenoxyethanol, chlorphenesin, and methylparaben, wherein the propylene glycol comprises from about 30% to about 45% of the complex, the phenoxyethanol comprises from about 22% to about 37% of the complex, the chlorphenesin comprises from about 11% to about 22% of the complex, and the methylparaben comprises from about 11% to about 22% of the complex;
(dd) about 0.03% to about 0.07% of trisodium EDTA;
(ee) about 0.40% to about 0.55% of benzophenone-4;
(ff) about 0.02% to about 0.04% of benzophenone-2;
(gg) about 1.05% to about 1.45% of titanium dioxide;
(hh) about 0.7% to about 0.9% of fragrance;
(ii) about 4.25% to about 5.7% of a micellar complex comprising horse chestnut extract, Crataegus extract, water, panthenol, propylene glycol, phospholipids, phenoxyethanol, glycosphingolipids, chlorphenesin, and cholesterol, wherein the horse chestnut extract comprises from about 9% to about 18% of the micellar complex, the Crataegus extract comprises from about 9% to about 18% of the micellar complex, water comprises from about 24% to about 36% of the micellar complex, the propylene glycol comprises from about 3% to about 9% of the micellar complex, the phospholipids comprise from about 3% to about 9% of the micellar complex, the phenoxyethanol comprises from about 3% to about 9% of the micellar complex, the glycosphingolipids comprise from about 3% to about 9% of the micellar complex, the chlorphenesin comprises from about 3% to about 9% of the micellar complex, and the cholesterol comprises from about 3% to about 9% of the micellar complex;

(jj) about 0.03% to about 0.07% of D&C Red #30 Lake; and (kk) about 0.005% to about 0.01% of FD&C Yellow #6 Aluminum Lake;

with water comprising the remainder of the skin cream composition.

* * * * *